United States Patent [19]

Sawyer

[11] 4,038,702
[45] Aug. 2, 1977

[54] ELECTROCHEMICAL AND CHEMICAL METHODS FOR PRODUCTION OF NON-THROMBOGENIC METAL HEART VALVES

[76] Inventor: Philip Nicholas Sawyer, 606 Third St., Brooklyn, N.Y. 11215

[21] Appl. No.: 399,466

[22] Filed: Sept. 21, 1973

[51] Int. Cl.$^2$ ................... A61F 1/22; A61F 1/24; C25F 1/04
[52] U.S. Cl. ........................... 3/1.5; 3/1; 204/129.1
[58] Field of Search ............ 3/1, 1.4, 1.5; 204/129.1

[56] References Cited

U.S. PATENT DOCUMENTS

| | | | |
|---|---|---|---|
| 2,412,186 | 12/1946 | Whitehouse et al. | 104/129.1 X |
| 2,429,676 | 10/1947 | Faust | 204/129.1 X |
| 2,440,715 | 5/1948 | Faust et al. | 204/129.1 X |
| 3,491,756 | 1/1970 | Bentov | 128/221 |
| 3,609,768 | 10/1971 | Ayres | 3/1 |
| 3,703,452 | 11/1972 | Beroff et al. | 204/129.1 |
| 3,723,754 | 3/1973 | Murayama et al. | 307/88 ET |

OTHER PUBLICATIONS

Prosthetic Heart Valves, by Brewer et al., pp. 198–202, pub. by Chas. C. Thomas, Springfield, Ill. (1969).
Young et al., Metal Finishing, May 1942, pp. 237, 238.

Primary Examiner—F.C. Edmundson
Attorney, Agent, or Firm—Roberts & Cohen

[57] ABSTRACT

A method of improving the operation of metal heart valves according to which the surfaces of the heart valves are treated to render more negative the electrochemical potential which the valve part will exhibit in blood or a blood-like fluid and to minimize surface non-homogenities. The surface is treated to obtain more particularly a negative surface potential which is generally homogeneous and more negative than + 100 mv/NHE by chemical polishing, electrochemical polishing or cathode cleaning.

1 Claim, 18 Drawing Figures

ELECTROCHEMICAL AND CHEMICAL METHODS FOR PRODUCTION OF NON-THROMBOGENIC METAL HEART VALVES

FIELD OF INVENTION

This invention relates to improvements in prosthetic services and more particularly to improvements in metal heart valves.

BACKGROUND

Repeated attempts have been made to develop durable prosthetic heart valves with excellent physiologic function which are free of thrombosis, infection, embolism, fibroplastic overgrowth, orifice occlusion, poppet sticking and so forth. Some of these attempts are reported in: Prosthetic Heart Valves, Lyman A. Brewer, III, M.D., editor Chas. C. Thomas Publisher, Springfield, Ill., 1969; Sauvage, L. R., Viggers, R. F., Berger, K., Roble, S. B. Sawyer, P. N., and Wood, S. J., Prosthetic replacement of the aortic valve, Chas. C. Thomas Publisher, Springfield, Ill., 1972; Spencer, F. C., Reed, E. R., Clauss, R. H., Tice, D. A., Ruppert, E. M., Cloth covered aortic and mitral valve prostheses: Experiences with 113 patients; and so forth.

That thrombosis is an interfacial or surface chemical phenomenon has been known since the beginning of the 19th Century. Reports on this phenomenon may be found in: Scudamore, C., Essay on the blood, Longman, Hurst, Rees, Orme, Brown, and Green, London 1824; Text-Book of Electricity in Medicine and Surgery, George Vivian Poore, Smith, Elder and Company, London 1876.

Approximately 20 years ago, fairly clear cut evidence became avialable that electrochemical phenomena were active in both the maintenance of vascular homeostasis and in the prevention of intravascular thrombosis (Sawyer. P. N., Pate, J. W., Bioelectric phenomena as etiologic factors in intravascular thrombosis, Surg., 34:491, 1953). Briefly stated, all mechanisms which subtract electrons from blood tend to induce thrombosis, while donation of electrons to blood tends to be antithrombogenic. This is discussed in: Sawyer, P. N., Brattain, W. H., Boddy, P. J., Electrochemicl precipitation of human blood cells and its possible relation to intravascular thrombosis: The National Acad. of Sci., 51:428, 1964; Sawyer, P. N., Wu, K. T., Wesolowski, S. A., Brattain, W. H., Boddy, P. J., Electrochemical precipitation of blood cells on metal electrodes; and aid in the selection of vascular prostheses, Nat. Acad. Sci., 53:294, 1964; and so forth.

Multiple studies have been carried out on metal tubes, wires, wires at set potential and wires permitted to come to their spontaneous potential without current flow both in vitro and in vivo. Discussions of these studies appear in: Sawyer, P.N., Brattain, W. H. Brattain, W. H., Boddy, P. J., A case for considering electrochemical criteria in the choice of materials used in vascular prostheses; Ibid 337-348; Sawyer, P. N., Srinivasan, S., Metallic and prosthetic devices as vascular wall substitutes, Biophysical and methods for evaluation, Biomed. Mater. Res., 1:83, 1967; Sawyer, P. N., Wu, K. T., Wesolowski, S. A., Brattain, W. H. Boddy, P. J., Long term patency of solid wall vascular prostheses, Arch. Surg., 91:735, 1965; and so forth.

These studies show that thrombosis on prosthetic surfaces is intimately related to the spontaneous potential of the metal in prosthetic valves, and ultimately to the homogeneity of surface charge and its sign of all insulator surfaces exposed to blood. This is set forth in: Sawyer, P. N., The effect of various metal interfaces on blood and other living cells, Ann. of N.Y. Acad. of Sci., 146:49, 1968; Sawyer, P. N., Srinivasan, S., Wesolowski, S. A., Berger, K. E., Campbell, A. A., Samma, A. A., Wood, S. J., Sauvage, L. R., Development and in vivo evaluation of metals for heart valve prostheses; Trans. Amer. Soc. Artif. Int. Organs 13:124, 1967.

Gradually, an experience has evolved, with the implantation of several hundred valves in dogs and calves in the tricuspid, mitral and aortic annuli by several investigators which has provided proof that valves can be made to display an increasing antithrombogenic tendency related not only to their corrosion potential, but also to their cleanliness at the time of implantation. This is seen in: Sawyer, P. N., Srinivasan, S., Lee, M. E., Martin, J. G., Murakami, T., and Stanczewski, B., Dependence of long term function of prosthetic heart valves on their interfacial potential; Proc. of II National Conf. on Prosthetic Heart Valves, Lyman A. Brewer, III, M. D., Editor, Charles C. Thomas, Publisher, Chap. 13:198, 1969; and so forth.

SUMMARY OF INVENTION

It is an object of the invention to provide an improved method for the improving of the performance of prosthetic devices in a blood containing environment such as may be encountered in the heart or in the vascular system.

It is a further object of the invention to provide for improving the electrochemical potential characteristics of prosthetic devices.

It is more particularly an object of the invention to provide methods for preparing heart valves for implantation.

Generally in achieving the above and other objects of the invention, there is provided a method of improving the performance of a prosthetic device in a bloody environment such as in the heart or in a vascular system, said method comprising treating the surface of the device to render more negative the electrochemical potential which the device will exhibit in blood or in a blood-like fluid and to increase the homogeneity of the surface charge.

More particularly, the principal prosthetic device with which the invention is particularly concerned is a metal heart valve or a part thereof and the method of the invention comprises treating the surface of such valve or part to improve the surface characteristics thereof.

In accordance with a feature of the invention, the surface of some metallic heart valves are treated to obtain a negative surface potential which is more negative than + 100 mv./NHE by chemical polishing, electrochemical polishing or cathodic cleaning.

When the surface is treated by chemical polishing, an acid bath is preferably employed. The acid bath is preferably and at least partly of phosphoric acid, sulphuric acid, chromic acid or nitric acid.

When the surface is treated by electrochemical polishing, the part is set up as an anode in a bath through which is passed a current in a range from about 10 to 100 amperes per square foot for about 1 to 5 minutes at about 60° to 110° C.

When the surface is treated by cathodic cleaning, it is treated in a bath in which the part is set up as a cathode and the bath is preferably acid or alkaline, and about 10 to 110 amperes/ft² are passed through the part for about 1 to 10 minutes with the bath being a temperature of about 60° to 110° C.

According to the invention, the part thusly treated is installed in a living body within twenty-four hours. If the part is not installed within twenty-four hours, it is preferably stored in a vacuum or inert atmosphere.

Other objects, features and advantages of the invention will be more clearly understood from the detailed description which follows hereinbelow as illustrated in the accompanying drawing.

DETAILED DESCRIPTION

Figure 1:
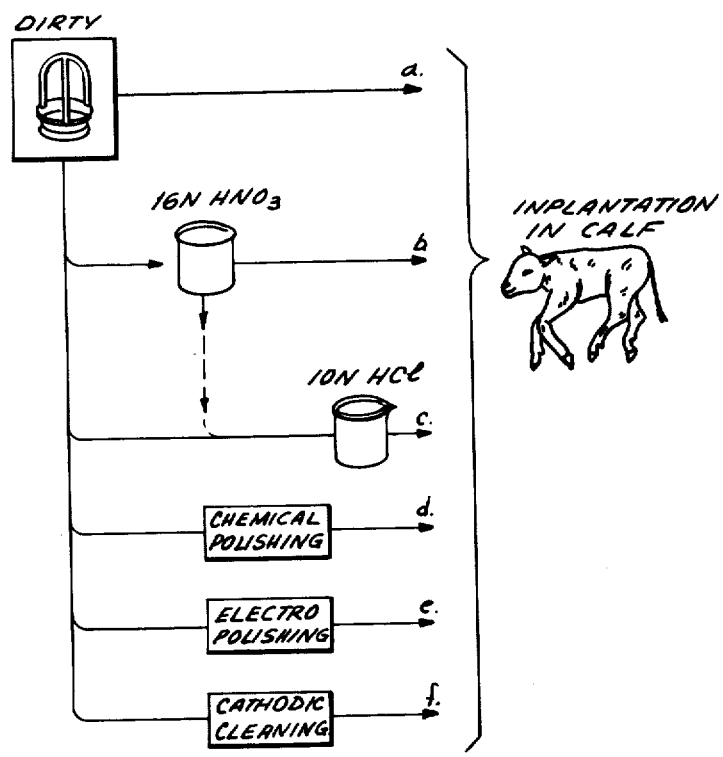
FIG. 1 diagrammatically illustrates the treatments which may be accorded a heart valve part before implantation, some of the techniques illustrated being provided in accordance with the invention.

Multiple valve castings including metals and alloys such as aluminum, Howmedica alloy XP 403, Smelloff-Cutter Titanium, Arwood Stellite 21, Starr-Edwards Stellite 21, and Arwood Copper Heart Valves will be described below. These metals span the spectrum of the electromotive series from highly corrosive to noble metals as shown by the following table:

ELECTROMOTIVE FORCE SERIES OF ELEMENTS
Compiled by Giles B. Cooke
Standard Electrode Potentials at 25° C

| Element | Iron | Electrode reaction | | Electrode Potential |
|---|---|---|---|---|
| Li | Li+ | Li = Li+ | +e | +2.9595 |
| Rb | Rb+ | Rb = Rb+ | +e | 2.9259 |
| K | K+ | K = K+ | +e | 2.9241 |
| *Sr | Sr++ | ½Sr = ½Sr++ | +e | 2.92 |
| *Ba | Ba++ | ½Ba = ½Ba++ | +e | 2.90 |
| *Ca | Ca++ | ½Ca = ½Ca++ | +e | 2.87 |
| Na | Na+ | Na = 0 Na+ | +e | 2.7146 |
| *Mg | Mg++ | ½Mg = ½Mg++ | +e | 2.40 |
| *Al | Al+++ | ⅓Al = ⅓Al+++ | +e | 1.70 |
| *Be | Be++ | ½Be = ½Be++ | +e | 1.69 |
| *U | U++++ | ¼U = ¼U++++ | +e | 1.40 |
| *Mn | Mn++ | ½Mn = ½Mn++ | +e | 1.10 |
| *Te | Te− | ½Te− = ½Te | +e | 0.827 |
| Zn | Zn++ | ½Zn = ½Zn++ | +e | 0.7618 |
| Cr | Cr++ | ½Cr = ½Cr++ | +e | 0.557 |
| *S | S− | ½S = ½S | +e | 0.51 |
| *Ga | Ga+++ | ⅓Ga = ⅓Ga+++ | +e | 0.50 |
| Fe | Fe++ | ½Fe = ½Fe | +e | 0.441 |
| *Cd | Cd++ | ½Cd 32 ½Cd++ | +e | 0.401 |

-continued
ELECTROMOTIVE FORCE SERIES OF ELEMENTS
Compiled by Giles B. Cooke
Standard Electrode Potentials at 25° C

| Element | Iron | Electrode reaction | | Electrode Potential |
|---|---|---|---|---|
| *In | In+++ | ⅓In = ⅓In+++ | +e | 0.336 |
| *Tl | Tl+ | Tl = Tl+ | +e | 0.330 |
| Co | Co++ | ½Co = ½Co++ | +e | 0.278 |
| Ni | Ni++ | ½Ni = ½Ni++ | +e | 0.231 |
| Sn | Sn++ | ½Sn = ½Sn++ | +e | 0.136 |
| Pb | Pb++ | ½Pb = ½Pb++ | +e | 0.122 |
| *Fe | Fe+++ | ⅓Fe = ⅓Fe+++ | +e | 0.045 |
| H₂ | h+ | ½H₂ = H+ | +e | 0.0000 |
| *Sb | Sb+++ | ⅓Sb = ⅓Sb+++ | +e | −0.10 |
| *Bi | Bi+++ | ⅓Bi = ⅓Bi+++ | +e | −0.226 |
| *As | As+++ | ⅓As = ⅓As+++ | +e | −0.30 |
| Cu | Cu++ | ½Cu = ½Cu++ | +e | −0.344 |
| *O₂ | OH− | OH³¹ = 1/6O₂ +½H₂O | +e | −0.397 |
| Po(18° C) | Po++++ | ¼Po = ¼Po++++ | +e | −0.40 |
| Cu | Cu+ | Cu = Cu+ | +e | −0.470 |
| I₂ | I− | I− = ½I₂ | +e | −0.5345 |
| *Te | Te++++ | 1/4Te = ¼Te++++ | +e | −0.558 |
| Ag | Ag+ | Ag = Ag+ | +e | −0.7978 |
| Hg | Hg++ | 2Hg = Hg₂++ | +2e | −0.7986 |
| *Pb | Pb++++ | ¼Pb = ¼Pb++++ | +e | −0.80 |
| *Pd | Pd++ | ½Pd = ½Pd++ | +e | −0.820 |
| *Pt | Pt | ¼Pt = ¼Pt++++ | +e | −0.863 |
| Br₂ | Br− | Br− = ½Br₂ | +e | −1.0648 |
| Cl₂ | Cl− | Cl− = ½Cl₂ | +e | −1.3583 |
| *Au | Au+++ | ⅓Au = ⅓Au+++ | +e | −1.360 |
| *Au | Au+ | Au = Au+ | +e | −1.50 |
| *F₂ | F− | F− = ½F₂ | +e | −1.90 |

*These values are doubtful but they indicate the relative activity of the elements and are therefore included.

1. Action of Metals on Salts. - Any metal will replace any other metal below it in the series thus:

Mg + FeSO₄ → MgSO₄ + Fe

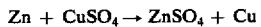

Zn + CuSO₄ → ZnSO₄ + Cu

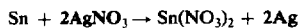

Sn + 2AgNO₃ → Sn(NO₃)₂ + 2Ag

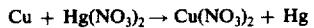

Cu + Hg(NO₃)₂ → Cu(NO₃)₂ + Hg

This is the fundamental principle of the Daniell Cell. The voltage of such a cell depends upon the difference between the electrode potentials of the metals employed. Thus the Zn-Cu couple gives a greater E.M.F. than the Zn-Pb couple or the Fe-Cu couple.

The valves described hereinafter as being treated according to the invention were in almost all instances implanted into the tricuspid annulus of calves and remained in place for periods longer than 7 months and in most instances for periods approaching 2 years; Kaplitt, M. J., Rubin, R. and Sawyer, P. N., A reinforced autogenous venous skirt: A new approach to the sewing ring problem is posthetic heart valves, Current Topics in Surg. 2:477, 1970.

The valves were treated in various ways prior to implantation as shown in FIG. 1. These methods included (a) non-cleaned or "dirty" valves; (b) the valves being placed for 30 seconds in a 16 normal nitric acid dip to produce a clean oxide surface (c) the valves being placed in a 10 normal hydrochloric acid dip to produce a clean surface (d) the valves being subjected to chemical or electrochemical polishing in special solutions (the solution composition is different for different metals (e) electropolishing with a potentiostat to maintain the metal valve cage at a given cathodic potential or (f) cathodic cleaning.

The ultimate goal of the invention is to provide a method for preparing a prosthetic device so that the same will be particularly suitable for use in a blood containing environment wherein the implantation of the prosthetic device will not result in thrombus nor in any embolism and due to which method the device will continue to function over a long period of time and will not produce fibroplastic overgrowth with respect to the sewing ring.

The prosthetic devices heretofore available were generally considered to be comparatively clean and acceptable for implantation purposes. However, these devices have resulted in situations wherein, after implantation, visible thrombus could be seen microscopically or grossly and it has been found that the thrombus formation compromises the prosthetic function. The prosthetic devices heretofore employed, although satisfactorily to a certain degree, combine, by the standards of the present invention, dirty surfaces with the corrosive properties of blood producing excessive pitting which is visible at the microscopic level. It is believed that a preferred maximum pitting does not exceed a diameter of 50=100 Angstrom. More important, however, the surfaces heretofore available in heart valves give a relatively positive and generally non-homogenous electrochemical surface potential in blood or in a blood-like fluid.

It is one of the objects of the invention to provide clean surfaces or, in other words, surfaces which are substantially more negative in potential and homogeneous than surfaces provided on heretofore available "dirty" prosthetic device surfaces.

More specifically, with reference to Stellite 21, this material before cleaning in accordance with the invention has a surface potential of about + 15 mv. whereas after cleaning in accordance with the invention, it will have an electrochemical surface potential of − 260 mv. as against a saturated calomel electrode.

Referring by way of further example to titanium prosthetic devices such as heart valves, when these are cleaned in accordance with previously available techniques and therefore are relatively dirty according to the standards of the instant invention, such devices will show a surface potential of + 100 to 200 mv. whereas, after having been cleaned in accordance with the invention, they will exhibit a surface potential of − 160 mv. as compared to a saturated calomel electrode. It will of course be understood that this is the surface potential exhibited in blood or in a blood-like fluid.

With further reference, by way of example, to stainless steel 309, when dirty this material will exhibit a surface potential of − 130 mv. whereas when cleaned in accordance with the instant invention, a surface potential of − 300 mv. will be achieved.

With still further reference to Stellite, this will present a non-homogeneous surface, when cleaned according to previously available techniques, of about + 10 mv. whereas, when cleaned according to the invention, a electrochemical surface potential in the order of minus 310 mv. will be exhibited in blood or in a blood-like fluid.

It has been found according to the invention that "dirty surfaces" are those with non-homogenieties in the surface potential of a prosthetic surface at the solid-liquid interface. The particles of oxide or the like which appear on this surface may be small but produce large surface potential differences. This has the effect of making the adjacent surface potential vastly more positive and therefore unacceptable according to the invention.

According to the invention, there are two general techniques which can be employed for cleaning prosthetic devices. These include cleaning and polishing techniques. The polishing technique is intended to smooth a surface in order that pits and protrusions should not exceed the limits specified hereinabove. The polishing technique includes chemical polishing in which no electrical current is involved and electrochemical polishing or electropolishing in which electrical current is involved. In electrochemical or electropolishing, the valve or valve part to be polished is set up as the anode. Baths are employed which may preferably be acid baths and which may or may not contain organic compounds. The acids which are preferably employed are phosphoric acid, sulfuric acid, hydrochloric acid, chromic acid ($CrO_3$) and nitric acid. In the event that electrochemical polishing is employed, the bath is preferably at a temperature of 60° – 110° C and 10 – 100 amperes/square foot are passed through the part being cleaned for a time period of about 1 – 5 minutes.

In the cleaning techniques of the invention, this generally indicates the removal of surface contamination and dirt. In heart valves, for example, this has to do with contamination of the valves due to dirt deposited on the wall from the environment and also to dirt and grease which might be present due to handling and/or storage.

Where a cathodic cleaning is employed in acordance with the invention, the article to be cleaned is the cathode. It is placed in an acid or alkaline solution such as a hydrochloric solution or a sodium hydroxide solution or in a sodium carbonate solution. The article to be cleaned is exposed to a current of about 10 – 100 amperes/$ft^2$ in a bath or solution of a temperature of about 60 – 100° C for approximately 1 to 10 minutes. In another type of cathodic cleaning empolyed in accordance with the invention the article to be cleaned is dipped in concentrated hydrochloric acid and maintained at a cathodic potential by means of a potentiostat for 5 – 15 minutes.

In further accordance with the invention, the part whih is cleaned as generally indicated above is preferably implanted in a living body within twenty-four hours and preferably in under twelve hours or is alternatively stored in a vacuum or in an inert gas.

A "dirty" valve according to the invention is a valve with a surface which deposits from a blood containing environment sufficient coagulatory materials or thrombus and other deposits and tissues such that, after a short period of implantation, physical thrombus is seen microscopically or grossly and the thrombus formation compromises prosthetic function. In addition, the combined dirty surface and corrosive properties of the blood or blood-like fluid produce excessive pitting visible at microscopic levels and having a diameter exceeding the maximum permissible 50 – 100 Angstroms diameter mentioned hereinabove. Furthermore, the "dirty surface" which has been referred to gives non-homogeneous electrochemical surface characteristics which are relatively positive and not within the limits which have already been mentioned.

Figure 2:
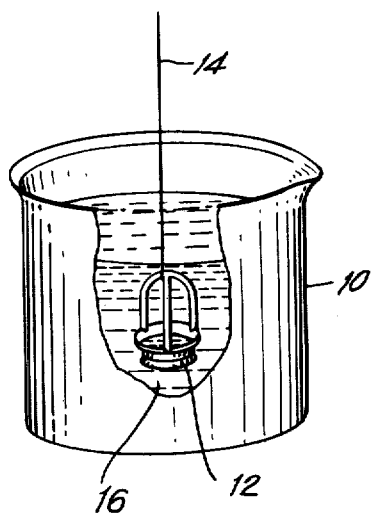
FIG. 2 diagrammatically illustrates the chemical polishing technique employed in accordance with the invention.

Appearing more particularly in FIG. 2 is a container 10 in which is suspended a valve part 12 by means of an electric line 14, the container 10 being provided with a bath 16 of the aforenoted composition. Herein the valve part is set up as the anode and the technique illustrated is the electrochemical polishing technique which otherwise has the limitations noted hereinabove, notably that the bath is maintained at a temperature of 60° - 110° C and preferably within the range of 70° - 90° C with a current of 10 - 100 amperes/ft$^2$ being passed through the valve part at 12 for a period of 1 - 5 minutes.

Figure 3:
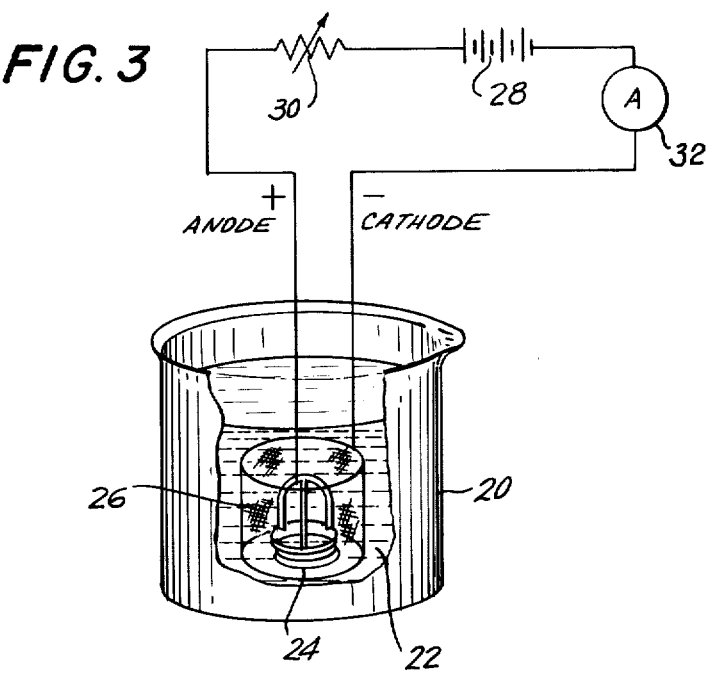
FIG. 3 diagrammatically illustrates the electropolishing technique employed in accordance with the invention.

FIG. 3 illustrates the electropolishing technique wherein is seen a container 20 within which is a bath or solution 22, the part 24 being cleaned being enclosed within a screen 26. The part 24 is maintained positive by a voltage source 28 passing current through a variable resistor 30, the current being measured by an ammeter 32. It will be noted that the screen 26 is maintained negative by the aforesaid voltage source 28.

Figure 4:
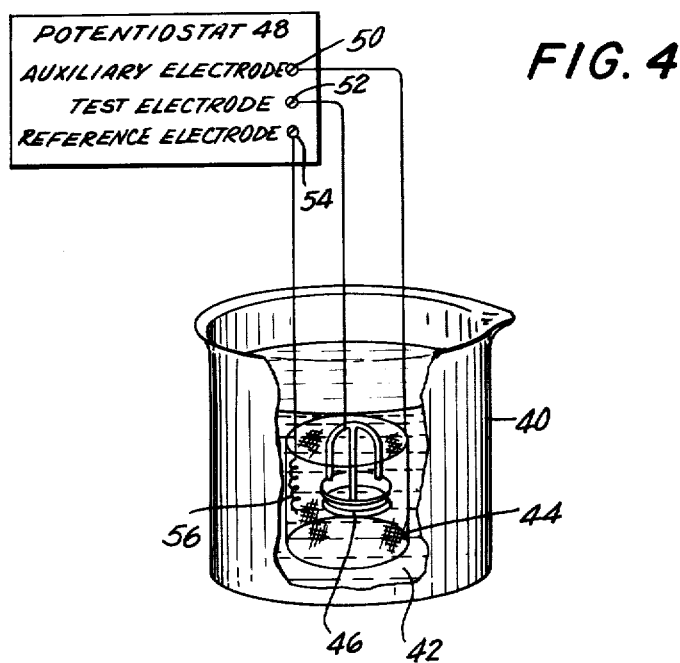
FIG. 4 illustrates the cathodic cleaning technique employed in accordance with the invention.

Cathodic cleaning is illustrated in FIG. 4 wherein can be seen a container 40 within which is a solution 42 there being suspended within the solution a screen 44 within which is a part 46 to be cleaned. A potential source 48 is employed having an auxiliary electrode 50, a test electrode 52 and a reference electrode 54. The test electrode 52 is connected to the part 46 whereas the electrode 54 is connected to a coil 56 contained within the screen 44.

Figure 5:
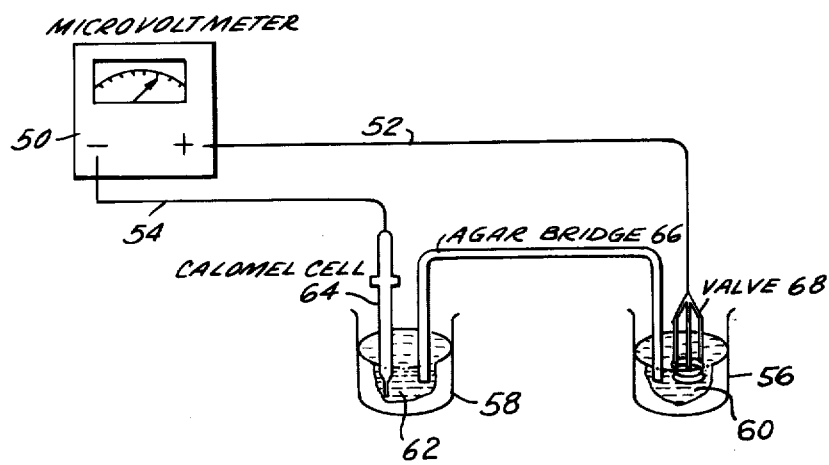
FIG. 5 illustrates diagrammatically a method for measuring spontaneous potential in blood in order to evaluate valve treatment in accordance with the invention.
Figure 6:
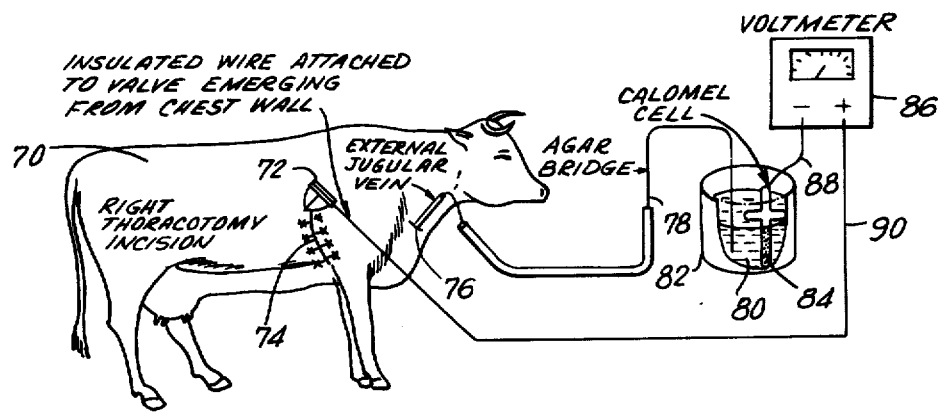
FIG. 6 illustrates an in vivo technique for the measurement of interfacial potential employed for evaluating valve implantation where the valve is prepared in accordance with the invention.

The potential differences on valves prior to cleaning, frequently during and following cleaning and in many instances at daily intervals following implantation were measured by a potentiometric measuring system as shown by FIGS. 5 and 6.

FIG. 5 illustrates a method of measuring spontaneous potential in blood or in a blood-like fluid. More particularly, in FIG. 5 appears a microvolt meter 50 connected by lines 52 and 54 to solution in respective containers 56 and 58. Container 56 includes animal blood 60 or a suitable blood-like fluid. Container 58 contains a saturated potassium chloride solution as indicated at 62. A calomel cell 64 is connected to line 54 and is partly immersed in solution 62. An agar bridge 66 is immersed partly in solution 62 and blood 60 forming a bridge between the containers or vessels 56 and 58. The valve which has been cleaned is indicated at 68 and is connected to the line 52. The microvolt meter measures the spontaneous electrochemical surface potential of the valve in the blood 60 or, in other words, measures the interface potential between the fluid and solid within the container 56.

FIG. 6 indicates an in vivo method for measuring interface potential. In FIG. 6 is more particularly indicated an animal 70 in which is implanted a heart valve 72. The incision for inserting the heart valve is indicated generally at 74 and an incision 76 permits the insertion of an extremity of bridge 78 into the juglar vein of the animal 70, the other end of the bridge 78 being immersed in a saturated potassium chloride solution 80 in container 82 which also receives a calomel cell 84.

A voltmeter 86 is provided with line 88 connected to calomel cell 84 and with line 90 connected to the valve 72. The indicated arrangement provides an in vivo method for measuring the solid-fluid interfacial potential or, in other words, the type of surface charge with which the invention is concerned.

Following cleaning, valves were implanted into the tricuspid annulus of heparinized calves of approximately 120 to 160 pounds in weight under total cardio pulmonary bypass. Following implantation, they passed a 30 day quarantine in a post operative animal care unit, and were then placed on a farm to be followed until the time indicated.

The valves were photographed upon removal and their potential differences in blood measured. They were then placed in buffered formalin solution. The potential was measured using the same potentiometer shown in FIG. 5. Thereafter, the metal surfaces, skirts and surrounding tissues were evaluated using light, electron and scanning electron microscopy.

The following reports discuss the effect of different surface treatments of the prostheses on the nature of thrombus deposits (in vivo) as revealed by scanning electron microscopy studies.

All the valves cast except the Starr-Edwards and the Smelloff-Cutter valves were Sawyer modifications of the classical Goodman, Berg, Stuckey, Dennis valve.

The valves will next be described in order of decreasing thrombus formation and therefore increasingly satisfactory function. More particularly, in the following FIGS. 7-9 will indicate controls with which relatively poor results were achieved while FIGS. 10 and 11 will illustrate surfaces with which intermediate results were received while the balance of the photomicrographs inclusive of FIGS. 12-16 will illustrate surfaces in connection with which very good results were achieved.

1. Arwood Copper Heart Valve - 10N HCl cleaned (as per (c) FIG. 1) - implanted 33 days (FIG. 7)

The copper valves displayed early thrombosis. Copper is a noble metal which becomes markedly positive in contact with blood. It is usually used as a "control" in this type of experiment because of its significant thrombogenic characteristics. On being cleaned in 10 normal hydrochloric acid, copper develops moderate pitting as seen at 10,000 magnification. Following implantation, there is progressive deposition of thrombus which is classical in structure, with marked fibrin, platelet, red cell, and white cell aggregates in the fibrin thrombus deposited on the valve, and skirt, ultimately trapping the ball in this instance. As expected, this represents a good demonstration of the thrombogenic propensity of markedly positive thrombogenic surfaces in which the metal has a virtually unlimited affinity-sink for electrons.

Figure 7:
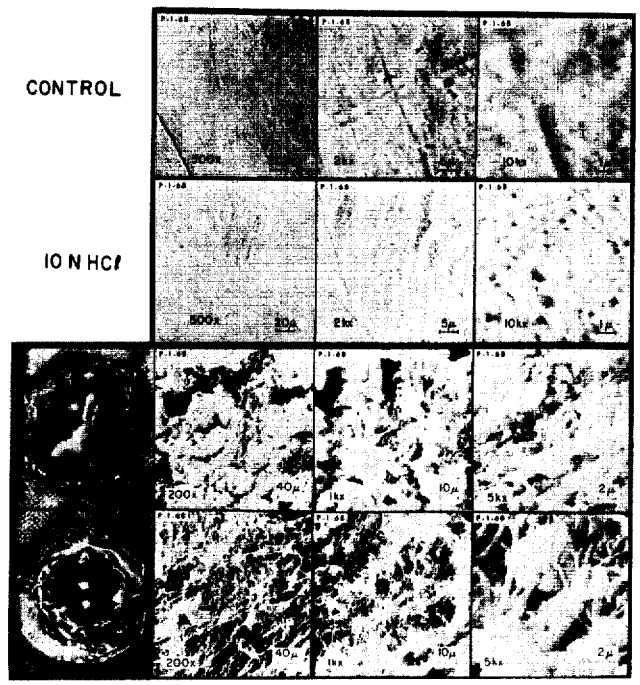
FIGS. 7–16 are photomicrographs illustrating control surfaces and valve surfaces prepared in accordance with various techniques provided in accordance with the invention.

In the top row of FIG. 7 is illustrated the control surface, from left to right, with magnifications of 500, 2000 and 10,000 times. The second row from the top of FIG. 7 illustrates the surface cleaned with a 10N hydrochloric acid solution. The magnifications corresponding to those of the uppermost row. The bottom two rows with the exception of the leftmost photographs illustrate the surfaces after implantation. The leftmost photographs illustrate photographs of the valve in entirety in installed position.

2. Starr-Edwards Cloth Covered Stellite 21 Heart Valve "6300" — uncleaned — implanted 7 months (FIG. 8)

The sequential series of scanning electron micrographs reveal sequential periods of thrombus deposition; on the metal of the valve as well as in the intersteces of the cloth covering the valve; organized into an abnormal fibrin-collagen type material; superimposed, progressive platelet deposition in the intersteces and fibrin formation along with sequential onion layering of thrombus on the valve struts.

Figure 8:

FIG. 8 shows "onion" layering of thrombus on the cloth covering the valve. The small figure at lesser magnification of this area shows the thrombus deposited on the cloth per se, removed from the valve.

FIG. 8 more particularly illustrates in the upper left-hand corner the installed valve as well as showing the installed valve in the lower left-hand photograph.

3. Starr-Edwards, Stellite 21 Ball Valve "6000" — uncleaned — implanted 255 days (FIG. 9)

There is marked irregularity of the surface with rapid, sequential deposition of fibrin, thrombus and platelets on the surface of dirty stellite 21 as shown in these FIGS. The mechanism of deposition relates to the uneven nature of the surface potential of the metal surface apparently produced by the omni-present oxides, sulfates, and other contaminants on the surface at implantation as shown in the first of this sequence of photographs.

Figure 9:
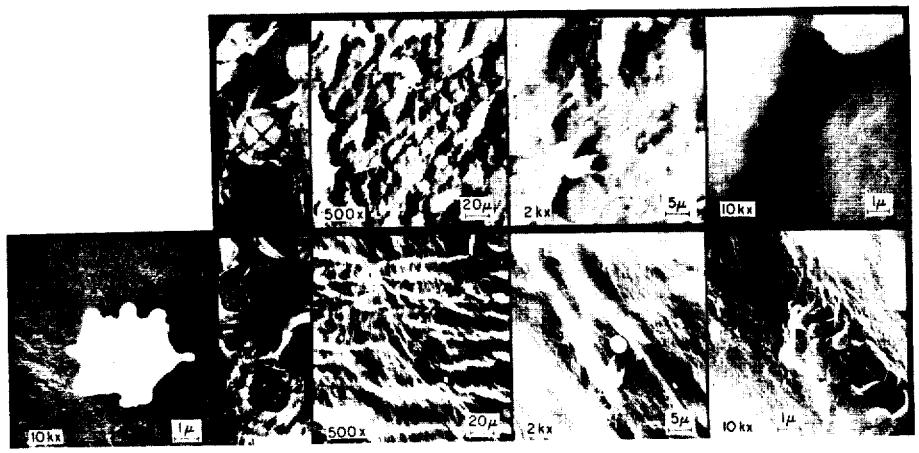

The upper row of FIG. 9 shows the surface of the prosthetic device prior to implantation at respective magnifications of 500, 2,000 and 10,000 times. The lower row shows the prosthetic device after it had been implanted with the three figures to the right in the bottommost row showing magnifications of 500, 2,000 and 10,000 times.

Figure 10:
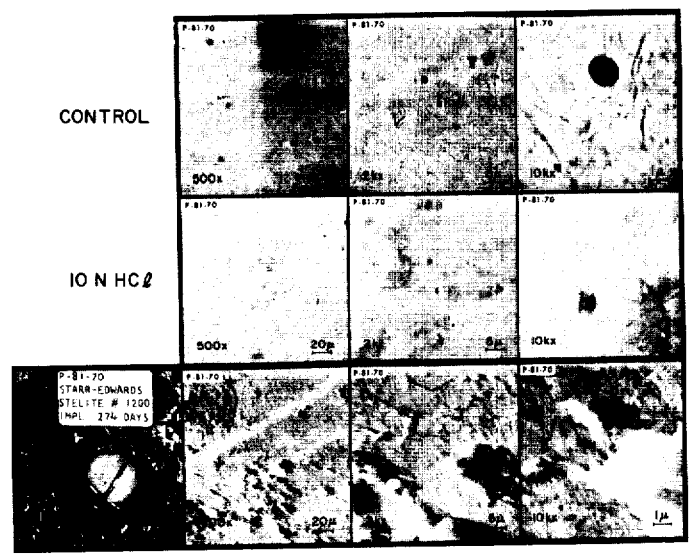

4. Starr-Edwards 1200 Stellite 21 Heart Valve — 10N hydrochloric acid cleaned — implanted 274 days (FIG. 10)

Cleaning with hydrochloric acid removes the dirty surfaces on the valve resulting in a progressively clean and oxide free metallic surface at implantation. There is little fibrin and few platelet colonies deposited following 274 days of implantation as shown in the last three pictures of this sequence magnified 10,000X.

The uppermost row in FIG. 4 is the control surface whereas the middle row shows the surface treated with a 10N hydrochloric solution. The lower row shows the surface after implantation with the exception of the leftmost figure which shows the valve in entirety. Starr-Edwards "1200", Stellite 21, Heart Valve — 10N HCl cleaned (FIG. 11)

On one strut of this prostheses there is rather marked formation of sequential onion layering of thrombus. Fibrous tissue and collagen were found. New organizing thrombus was also found between the valve strut and the ventricular septum. The thrombus in this instance possibly relates to the close approximation of the valve strut to the ventricular wall.

Figure 11:
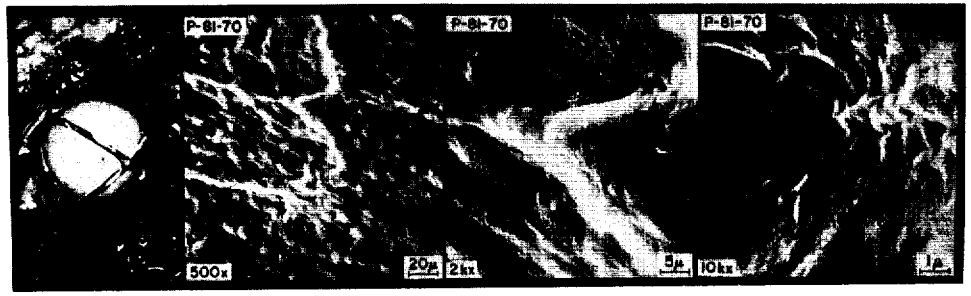

FIG. 11 with the exception of the leftmost photograph illustrates the surface after implantation whereas the leftmost figure shows the heart valve in its implanted position.

5. Starr-Edwards 37 1200" Stellite 21 Valve — cathodically cleaned implanted 604 days (FIG. 12)

The Starr-Edwards cathodically cleaned valve was intrinsically free of surface contaminants with some pitting at the time of implantation as shown in the second three shot sequence at 10K magnification. There is some deposition of fibrin and platelet colonies on this metal at two years with some thrombus on the apex of the valve extending down to a corda tendenae lateral to the valve. Following serial examination by light and electron microscopy this thrombus was found to have developed post mortem.

Figure 12:
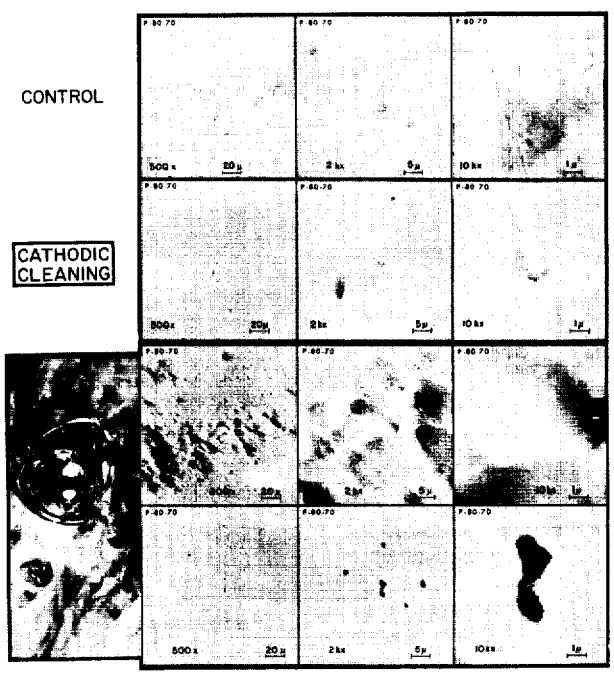

In FIG. 12, the upper control row shows minimal dirt with some pitting at implantation. Following cathodal cleaning, the surface appears both oxide and dirt-free with little residual pitting in the second row from the top.

Following implantation, the lower two rows of FIG. 12 are photographs of post morten thrombus from one strut of the valve. The total absence of thrombus and platelet-fibrin thrombi on the majority portion of the valve is shown in the lower row to 10K magnification. The residual pitting should be noted.

6. Arwood Stellite 21 — Sawyer Heart Valve — a cathodically cleaned — implanted 503 days (FIG. 13)

Cathodic cleaning of the Stellite 21 heart valve provided by Arwood produced increased pitting with essentially total cleanliness of the valve up to 10K at the time of sacrifice 503 days after implantation. There is almost no thrombus deposited on the surface of this valve at any point that is elucitable by either direct vision, light microscopy or scanning electron microscopy up to 10K magnification.

Figure 13:
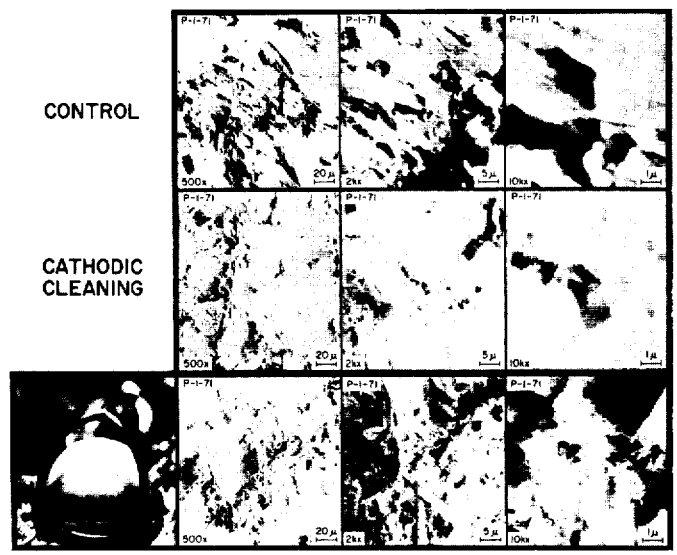

FIG. 13 shows a very pitted, porous Arwood cast Stellite 21. In FIG. 13, the top control row appears. The second from top row shows the results of cathodic cleaning which partially removes the pitting prior to implantation. The bottom row shows the relatively thrombus-free, platelet-free metal surfaces following 503 days of implantation shown at 10K magnification in the lower right hand corner at 503 days. Pitting per se is apparently not an obligatory indication for massive thrombus formation, which appears to depend on the presence of dirt, oxide and potential gradients.

Figure 14:
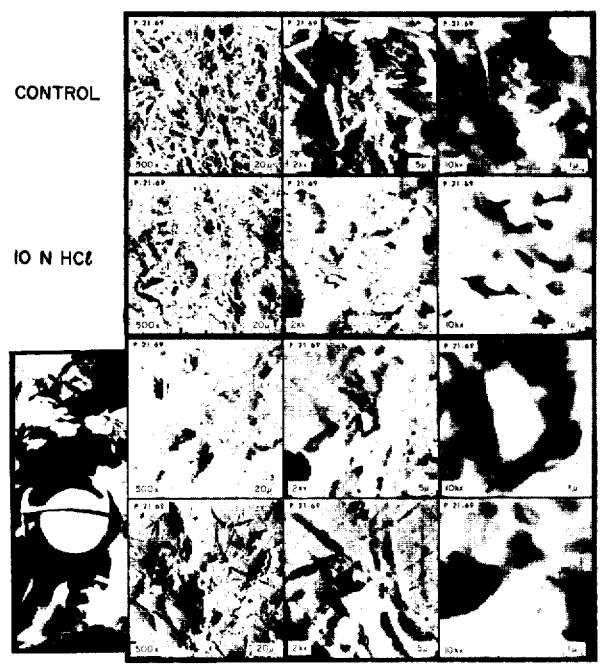

7. Arwood Aluminum Sawyer Heart Valve — cleaned in 10 normal HCl — implanted 765 days (FIG. 14)

Ten normal HCl produces rather marked pitting of the very porous, ultra pure aluminum valve, which, however, remains free of thrombus for its implantation period of 765 days in spite of oxidation on the surface as shown by the aluminum oxide in the higher magnifications in the lower two rooms of this sequence of photographs at 10K.

Electron microscopy reveals that a 0.01u layer of aluminum oxide covers the implanted clean aluminum valve. No visible cells are seen adjacent to this layer for distances approaching 0.7u. Thus, it is close to impossible for thrombus to deposit on the clean aluminum oxide surface.

Figure 15:
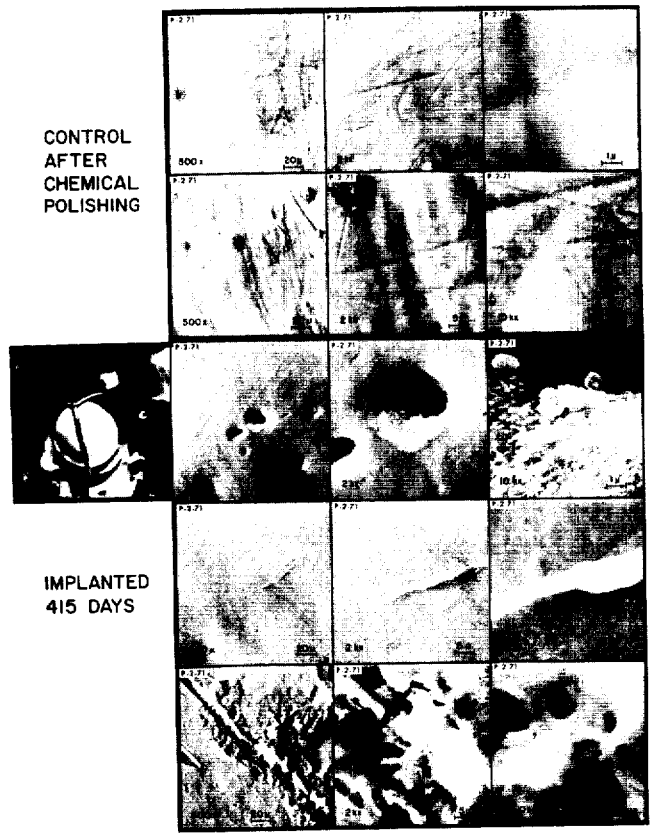

8. Arwood Aluminum Sawyer Ball Valve Chemically Polished — implanted 415 days — (FIG. 15)

Figure 16:
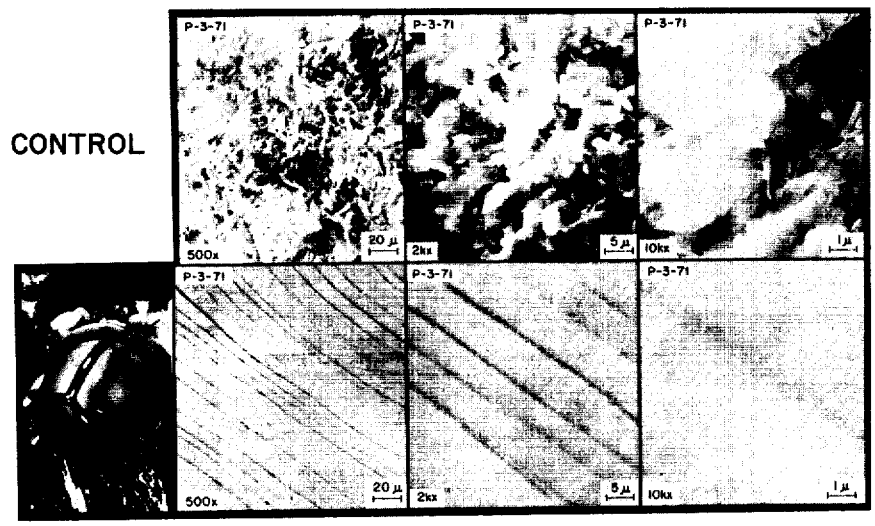

Chemically polished aluminum is increasingly free of pitting and remains totally free of visible thrombus deposition, platelet colonization, or any other form of abnormal surface characteristic for periods up to 415 days of implantation as shown in this sequence of figures. The bottom three rows of FIG. 15 show the surface after implant. This good result is also true of the electro polished aluminum implanted 82 days (FIG. 16).

9. Electropolished Aluminum — Sawyer Valve- implanted 82 days — (FIG. 16)

Electropolishing produces an extraordinary clean aluminum oxide thrombus free surface.

Available evidence indicates that the exposure to blood of homogenously charged, "clean" negative surfaces at potentials more negative than +100 mv/NHE is essentially antithrombogenic. In addition, the more capable a process is of producing "ultra clean" and "dirt-free" negatively charged surfaces, the more certain will be the production of a long term thrombus free surface.

Calves are more prone than man to produce thrombus, convert fibrinogen to fibrin and deposit fibrous tissue on a prosthetic surface during healing. The prosthetis will heal at approximately 10–20 times the rate achieved in humans. When ultra clean surfaces are implanted in the tricuspid annulus, a site very prone to produce thrombus on prosthetic valves results. It is seen that exposure to blood following careful implantation of these clean prostheses produces a surface which is essentially free of thrombus formation. No anticoagulant was used in any of the animals following initial implantation.

Special preparation of valve surfaces as disclosed herein is of inestimable importance in maintaining the antithrombogenic characteristics of metal or metal alloy valve and ball surfaces. This further reduces the tendency for infection since lessened thrombus deposition will reduce the bacterial substrate as well and should ultimately make the surface more acceptable for long term use in humans.

The following tables show the composition of materials involved in tests carried out in developing the invention.

| STAINLESS STEEL 304 | | STAINLESS STEEL 309 | |
|---|---|---|---|
| ELEMENT | % | ELEMENT | % |
| C | 0.03 | C | 0.05 |
| Si | 0.15-0.42 | Si | 0.83 |
| P | 0.017 | P | 0.21 |
| S | 0.016 | S | 0.019 |
| Cr | 19.0 | Cr | 23.0 |
| Mn | 0.74-0.77 | Mn | 0.99 |
| Fe | BAL | Fe | BAL |
| Ni | 8.70-11.0 | Ni | 12.58 |

| INCONEL | | HASTALLOY | |
|---|---|---|---|
| ELEMENT | % | ELEMENT | % |
| C | 0.19 | C | 0.06 |
| Si | 2.01 | Si | 0.68 |
| Cr | 15.55 | V | 0.40 |
| Mn | 0.46 | Cr | 0.20 |
| Fe | 6.31 | Mn | 0.77 |
| Co | 0.06 | Fe | 4.86 |
| Ni | BAL | Ni | BAL |
| Nb | BAL | Mo | 27.91 |
| Ta | 2.8 | | |

| ALUMINUM | | STELLITE 21 | |
|---|---|---|---|
| ELEMENT | % | ELEMENT | % |
| Mg | .001 | C | .25 |
| Al | 99.992 | Si | 1.0 |
| Si | .001 | Cr | 27.0 |
| Mn | .001 | Mn | 1.0 |
| Fe | .001 | Fe | 3.0 |
| Cu | .004 | Co | Bal |
| | | Ni | 2.5 |
| | | Mo | 5.5 |

| N-155 | | COPPER | |
|---|---|---|---|
| ELEMENT | % | ELEMENT | % |
| C | .2 | Be | .00001 |
| Si | 1.0 | B | .1 |
| Cr | 21.0 | Mg | .001 |
| Mn | 2.0 | Al | .00001 |
| Fe | bal | Si | .001 |
| Co | 20.0 | Cn | .001 |
| Ni | 20.0 | Mn | .00001 |
| Mo | 3.0 | Fe | .01 |
| W | 2.5 | Ni | .001 |
| | | Cu | bal |
| | | Z | .001 |
| | | Ag | .01 |
| | | Pb | .001 |
| | | Bi | .001 |

| VITALLIUM ALLOY P401C | | VITALLIUM ALLOY P103C | |
|---|---|---|---|
| ELEMENT | % | ELEMENT | % |
| C | 0.20-0.35 | C | 0.05-0.15 |
| Si | 1. | Si | 1. |
| Cr | 27.-30. | Cr | 19.-21. |
| Mn | 1. | Mn | 2. |
| Fe | 0.75 | Fe | 3. |
| Co | BALANCE | Co | BALANCE |
| Ni | 0.75 | Ni | 9.-11. |
| Mo | 5.-7. | W | 14.-16. |

The following is a summary of the known techniques which are put to a novel use in accordance with the invention:

A. Electropolishing is an electrochemical process. The material to be polished is made the anode (positive electrode) in a solution of special composition (usually a mixture of phosphoric, chromic, and hydrochloric acids with glycerol) and current is passed (e.g., D.C. current of 50–500 amp/ft$^2$).

An example of a composition of solution and condition for the electropolishing of aluminum is as follows:

| | |
|---|---|
| $H_2SO_4$ | 4.7% |
| $H_3PO_4$ | 75% |
| $CrO_3$ | 6.5% |
| Current | 150 Amp/ft$^2$ |
| Temp. | 175 – 180° F |

Reference is made to Metal Finishing Guidebook - 1972 - page 518.

B. Chemical Polishing is similar to electropolishing in that solutions are used to dissolve the roughness of the metal surfaces, but no current is passed. The article is dipped in a hot solution of a mixture of acids (usually $H_3PO_4$, $H_2SO_4$, HCl, $CH_3COOH$,) at 80°–100° C for ½ to 5 minutes.

Both Chemical and Electropolishing (also called electrochemical polishing) produce bright mirror like smooth surfaces which are stain free, while mechanically polished surfaces have a layer of fused oxide and polishing compounds called the Beilbey layer. This fused surface can interfere with the function of a fused surface can interfere with the function of a prosthetic material as explained above.

Figure 17:
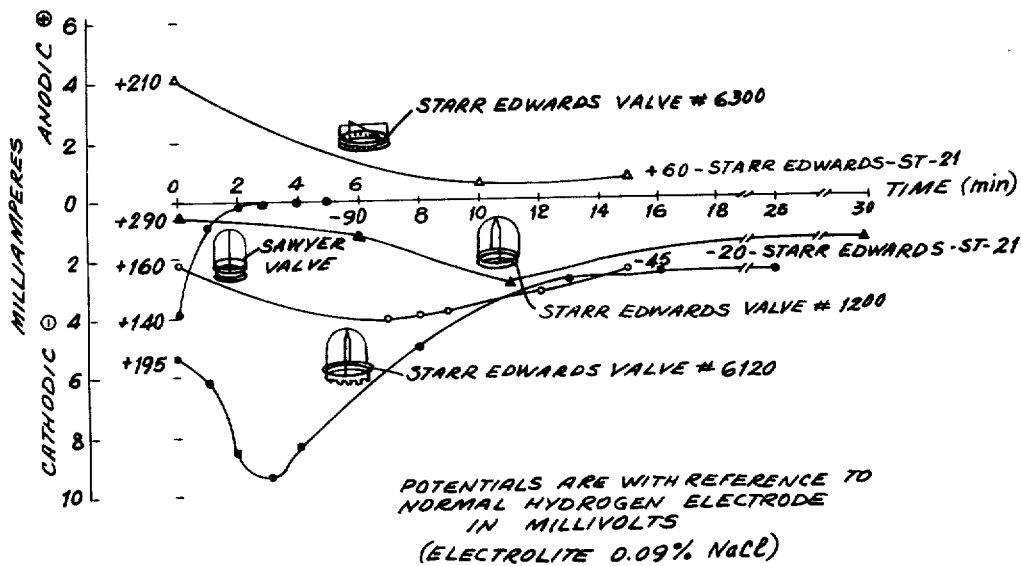
FIGS. 17 and 18 are charts relating to cathodic cleaning employed in accordance with the invention.
Figure 18:
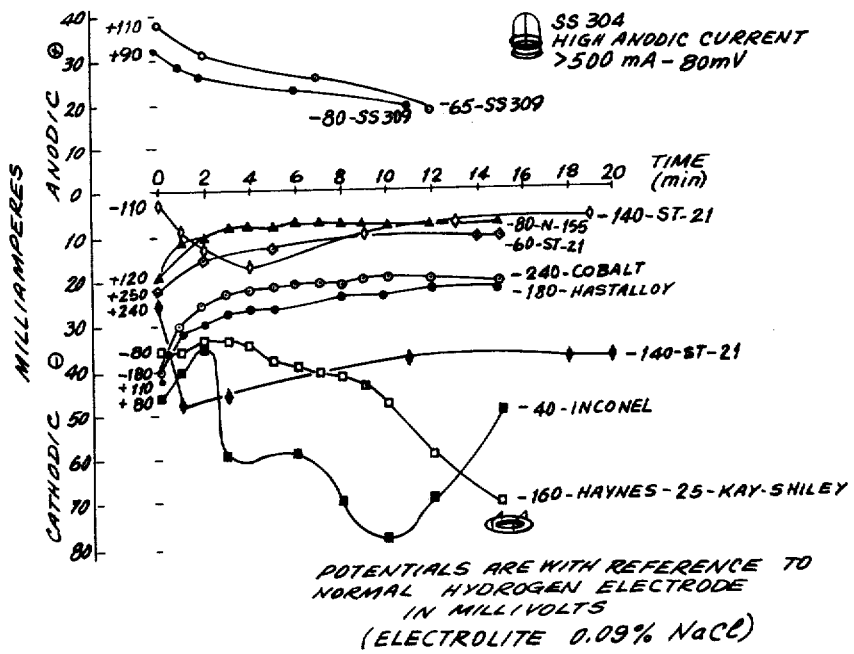

C. Cathodic Cleaning removes surface contaminants such as oxides, grease, etc. An article can be cathodically cleaned in an alkaline bath by making it the cathode and passing a high D.C. current (50–100 amp) through it for a few minutes. The vigorous hydrogen evolution dislodges any mechanically adhering dirt and grease. The cathodic cleaning used involved a special process called potentiostatic cleaning. The article to be cleaned (prosthetic metal heart valve) is dipped in concentrated HCL and is maintained at a cathodic potential with respect to an electrode (silver-silver chloride electrode) for 15 minutes. Any surface contaminants are dissolved and removed. FIGS. 17 and 18 show the types of current-time curves obtained where the metal is maintained at a constant cathodic potential (−100mv w.r.t. AgAgCl electrode). It is seen that for the same alloy, Stellite, three different valves show three types of I-T behavior though the curves after 15 minutes are similiar. This reveals varying amounts of surface contaminants on three different valves.

Preliminary results of similar study with valves of different metals and alloys are shown in FIG. 18.

With respect to pitting, this is a form of highly localized corrosion in chloride solutions (e.g., iron in NaCl). Pitting results in some cases where the metal (Stellite, stainless steels) is dipped in Conc, HCl either with or without cathodic current. Pitting, is to be avoided insofar as this increases the surface area susceptible to thrombus formation. However, a lightly pitted (seen at high magnification in scanning electron microscopy) HCl cleaned prosthetic surface will have a much greater chance of successful function in an animal than an "unclean" valve.

In connection with the processes of the invention as set forth hereinabove, it is preferred that no foreign particles be present on the surfaces of the valves thusly treated as might be seen by scanning with an electron microscope. However, as a preferred rule, the surfaces should have no more than two foreign particles not exceeding 0.5 microns in maximum diameter per 25 square microns of surface. If this rule is observed, non-thrombogenic metal heart valves will be obtained. If this limitation is slightly exceeded, valves of improved characteristics may be obtained provided that the number of foreign particles is minimized. However, for vastly superior results, the limitations mentioned hereinabove should be observed.

What is claimed is:

1. A prosthetic device including a metal structure having a metal surface, said metal surface being electrolytically treated to render more negative and homogeneous the electrochemical surface charge which the surface will exhibit in blood or a blooklike fluid, said surface having thereon no more than two foreign particles not exceeding 0.5 microns in maximum diameter per 25 square microns of surface.

* * * * *